United States Patent [19]
Commereuc et al.

[11] Patent Number: 5,811,619
[45] Date of Patent: Sep. 22, 1998

[54] METHOD OF PRODUCTION OF IMPROVED PURITY LIGHT ALPHA OLEFINES BY OGLIOMERISATION OF ETHYLENE

[75] Inventors: Dominique Commereuc, Meudon; Yves Glaize, Saint Symphorien d'Ozon; Francois Hugues, Vernaison; Lucien Saussine, Croissy sur Seine, all of France

[73] Assignee: Institut Francais du Petrole, France

[21] Appl. No.: 513,982

[22] PCT Filed: Jan. 13, 1995

[86] PCT No.: PCT/FR95/00044

§ 371 Date: Nov. 16, 1995

§ 102(e) Date: Nov. 16, 1995

[87] PCT Pub. No.: WO95/19332

PCT Pub. Date: Jul. 20, 1995

[30] Foreign Application Priority Data

Jan. 14, 1994 [FR] France .................................. 94 00453

[51] Int. Cl.$^6$ ....................................................... C07C 2/02
[52] U.S. Cl. .......................... 585/520; 585/527; 585/530; 585/532
[58] Field of Search ...................... 585/520, 530, 585/532, 527

[56] References Cited

U.S. PATENT DOCUMENTS

| | | | |
|---|---|---|---|
| 3,355,510 | 11/1967 | Cannell et al. | 585/512 |
| 3,384,678 | 5/1968 | Stapp | 585/530 |
| 3,642,932 | 2/1972 | Johnson | 585/512 |
| 4,006,199 | 2/1977 | Isa et al. | 585/532 |
| 4,377,720 | 3/1983 | Langer | 585/512 |
| 4,434,313 | 2/1984 | Langer, Jr. | 585/512 |
| 4,886,933 | 12/1989 | Shiraki et al. | 585/522 |
| 5,043,515 | 8/1991 | Slaugh et al. | 585/512 |
| 5,116,795 | 5/1992 | Fries | 585/512 |
| 5,260,500 | 11/1993 | Shiraki et al. | 585/520 |
| 5,292,979 | 3/1994 | Chauvin et al. | 585/530 |
| 5,345,023 | 9/1994 | Chauvin et al. | 585/532 |
| 5,496,783 | 3/1996 | Chauvin et al. | 502/123 |

FOREIGN PATENT DOCUMENTS

| | | | |
|---|---|---|---|
| 0 320 571 | 6/1989 | European Pat. Off. | C07C 2/30 |
| 0 578 541 | 1/1994 | European Pat. Off. | C07C 2/30 |

OTHER PUBLICATIONS

Patent Abstracts of Japan, vol. 15 (289), (C–852), 23 Jul. 1991.

Primary Examiner—Mark L. Bell
Assistant Examiner—Patricia L. Hailey
Attorney, Agent, or Firm—Millen, White, Zelano & Branigan, P.C.

[57] ABSTRACT

For obtaining of improved purity of light alpha olefines produced by oligomerization of ethylene, the ethylene is placed in contact with a catalyst obtained by mixture of a zirconium compound with an organic compound selected from the class of acetals and ketals and with a chlorinated or brominated aluminium hydrocarbyl compound, and that the raw oligomerization effluent is firstly treated with an amine, then subjected to vaporization so as to collect the alpha olefines in the vaporized fraction.

20 Claims, No Drawings

METHOD OF PRODUCTION OF IMPROVED PURITY LIGHT ALPHA OLEFINES BY OGLIOMERISATION OF ETHYLENE

BACKGROUND OF THE INVENTION

The subject-matter of the present invention is a method of production of improved purity light alpha defines by oligomerisation of ethylene by means of a specific catalyst (as described in French patent application no. 92/08658 of 9 Jul. 1992) of the Ziegler type, then destruction of said catalyst by injection of an amine followed by vapourisation of the effluent obtained.

More precisely, said catalyst is obtained by mixture:

of a zirconium compound with the formula $ZrX_xY_yO_z$ in which X is an atom of chlorine or bromide, Y is a radical selected from the group formed by $RO^-$alkoxys, $R_2N^-$aminos, and $RCOO^-$carboxylates, where R is a hydrocarbyl radical having 1 to 30 carbon atoms, x and y can have whole values from 0 to 4 and z equals 0 or 0.5, the sum of x+y being equal to 4, with an organic compound with the formula $(R_1')(R_2')C(OR_1)(OR_2)$ in which $R_1'$ and $R_2'$ are constituted by one atom of hydrogen or a hydrocarbyl radical having 1 to 30 carbon atoms, and $R_1$ and $R_2$ are hydrocarbon radicals having 1 to 30 carbon atoms, and with an aluminium compound with the formula $AlR''_nX_{3-n}$ in which R'' is a hydrocarbyl radical having 1 to 6 carbon atoms, X is an atom of chlorine or bromine, and n is a number between 1 and 2.

This catalyst is thus obtained by mixture of a zirconium compound, such as for example zirconium tetrachloride, with an organic compound selected from the class of acetals and ketals, resulting from the condensation of an aldehyde or of a ketone with a monoalcohol or a polyalcohol, such as for example 2,2-bis(2-ethylhexyloxy)-propane, and with a chlorinated or brominated compound of aluminium hydrocarbyl, such as for example aluminiumethylsesquichloride.

The method according to the present invention proposes a specific method for destruction of the oligomerisation catalyst described hereinabove.

In an industrial implementation of a method of homogeneous catalysis, in addition to the management of the reaction itself, there is the problem of the separation and isolation of products from the raw reaction mixture, and in particular of the catalyst, which is totally soluble in the reaction mixture.

In the case of the ethylene oligomerisation reaction, two methods can be utilised to this end:

removal of the catalyst before distillation of the hydrocarbons, either by precipitation and filtration or centrifuging, or by two-phase extraction, for example through water, direct distillation of the hydrocarbons, unconverted ethylene, 1-butene, 1-hexene, 1-octene, 1-decene and higher oligomers, which leaves the catalyst in the bottom of the distillation, still soluble, but concentrated in a fraction of heavy oligomers, as well as the polymer possibly produced as a secondary product.

Nevertheless, whatever the method used, it has been observed that in practice either the treatment with an aqueous phase or the prolonged contact between the oligomers and the catalyst in the reboilers of the distillation columns causes secondary reactions such as chlorination which are detrimental to the quality of the products. It is therefore desirable to destroy the activity of the catalyst beforehand, which can most often be carried out by addition of a base.

Thus the destruction of zirconium based ethylene oligomerisation catalysts by the addition of an anti-polymerisation reaction agent and of an amine at the end of the reaction has been described in U.S. Pat. No. 4,396,788, U.S. Pat. No. 4,434,312, U.S. Pat. No. 4,442,309 and U.S. Pat. No. 4,486,615 with the object of preventing the formation of connected secondary products, and in the case of EP 241 596 of preventing the formation of chlorinated by-products. The use of an aqueous solution of soda or ammonia together with or without the addition of an amine is mentioned in the patents described hereinabove as well as in EP 328 728 and JP03 103 406.

In EP 320 571, the product of the oligomerisation reaction is subjected to an operation separating the residual ethylene (called flashing), said operation being accompanied by precipitation of the polymer. The polymer is crushed and the mixture obtained is admixed with an amine so as to de-activate the catalyst. Distillation allows the olefinic compounds to be retrieved.

The decomposition of the ternary catalyst constituted by a mixture of a zirconium compound with an acetal or ketal and with an aluminium hydrocarbyl chloride by a neutral aqueous phase with pH 7 produces alpha olefines which are contaminated by the presence of chlorinated organic compounds. Applied to this same catalyst, the methods such as described hereinabove reveal themselves to be of little effect, as although they effectively reduce the proportion of chlorinated compounds in the oligomers, it still remains far too high for the normal applications of these olefines.

SUMMARY OF THE INVENTION

The invention also relates to a method for the destruction and specific separation of the ternary ethylene oligomerisation catalyst constituted by the mixture of a zirconium compound with an acetal or ketal and an aluminium hydrocarbyl chloride. It has been found that undesirable reactions, particularly the chlorination of the alpha olefines produced, can be almost completely stopped if the raw oligomerisation effluent is subjected to the following treatments, in order, before any fractional distillation:

1) introduction of at least one amine into the oligomerisation reactor effluent,
2) vapourisation of the effluent treated with the amine, either by increasing the temperature or by lowering the pressure, or by simultaneous action upon the temperature and the pressure, so as to collect to alpha olefines in the vapourised fraction.

The amines which may be used according to the invention are preferably primary or secondary amines with the general formula $R_1R_2NH$, in which $R_1$ is hydrogen or a hydrocarbonic radical and $R_2$ is a hydrocarbonic radical. $R_1$ and $R_2$ together can represent an alkylene radical. The hydrocarbonic radical can be aliphatic, cycloaliphatic or aromatic and has 1 to 22 carbon atoms.

Ammonia is unsuitable, as the comparative example below will show.

For practical reasons, it is desirable for the amine vapour pressure to be low so that it does not contaminate the alpha olefines in any appreciable manner during the distillation and/or redistillation thereof. For this reason amines are preferably used which have in all at least 6 carbon atoms, for example from 6 to 22. Among the amines, cyclohexylamine, ethyl-2-hexylamine, laurylamine, stearylamine, oleylamine, aniline, N-methyl aniline, dibutylamine, didecylamine, mixtures obtained from natural fatty substances, for example tallow, palm oil or copra oil, are mentioned in particular.

The amine is preferably added at the temperature at which the oligomerisation reaction takes place, that is to say between 20° and 180° C. and preferably between 40° and 150° C., or otherwise at a different temperature, 20 to 30 degrees more or less than the reaction temperature.

The quantity of amine added is such that the molar ratio between the amine and the aluminium compound contained in the reaction mixture is between 0.1:1 and 20:1, and preferably between 1:1 and 10:1.

The vaporisation of the raw effluent treated with the amine can be produced either by raising the temperature or by reducing the pressure, or by simultaneous action upon the temperature and the pressure. The range of useable temperatures and pressures depends upon the numerical distribution of carbon of the alpha olefines produced.

It is desirable to have a maximum amount of vapourisation, for example vapourisation of at least 90% of the volume of the effluent treated with the amine, and preferably 95% or more, so as to limit the quantity of discharge which has to be processed according to environmental regulations. Nevertheless, this must not lead to a prohibitively high vapourisation temperature, which is indeed detrimental to the thermal stability of the olefines. Preferably a vapourisation temperature less than or equal to 250° C. is kept to, and preferably 200° C.

The heavy products resulting from vapourisation and containing the de-activated catalyst may be incinerated or processed in any manner conforming to environmental standards.

The vapourised oligomers are, according to requirements, directed towards a system of distillation columns which allows the separation on the one hand of the unconverted ethylene of the oligomers, which ethylene can be returned to the oligomerisation reactor, then on the other hand of the oligomers themselves.

The following examples illustrate the invention without limiting the scope thereof.

EXAMPLE 1

$2.10^{-3}$ moles of sublimated zirconium tetrachloride is transferred, protected from humidity, into a 100 ml glass flask placed in an inert atmosphere, then 45 ml of dried and de-aerated toluene is injected by means of a hypodermic syringe. $2.10^{-3}$ moles of 2,2- bis(2-ethylhexyloxy)-propane in solution in 5 ml of toluene is added to the white suspension agitated at ambient temperature by means of a bar magnet. After several minutes, the zirconium chloride dissolves and the colour of the homogeneous solution thus obtained changes from pale yellow to orange, indicating the formation of a complex compound.

In order, 5 ml of the solution of the prepared complex compound of zirconium described above, that is to say $0.2.10^{-3}$ moles of zirconium, 50 ml of heptane and then $1.2.10^{-3}$ of aluminiumethylsesquichloride $Al_2Et_3Cl_3$ in solution in 10 ml of heptane is introduced in an argon atmosphere and at ambient temperature into a stainless steel autoclave with a useable volume of 250 ml, equipped with a double jacket allowing the temperature to be regulated by circulation of water or oil.

The temperature is then brought to 90° C. while introducing ethylene into the autoclave so as to maintain a constant pressure of 6 MPa. After 2 hours of reaction, the introduction of ethylene is ceased.

Then 0.55 g, that is to say $4.28\ 10^{-3}$ of ethyl-2-hexylamine in solution in 3 ml of toluene is injected into the autoclave under pressure, by means of a lock chamber which can be brought to a pressure greater than that of the autoclave. This corresponds to an amine/Al ratio equal to 1.78 molar.

The autoclave is then emptied by means of an internal tube reaching down to the bottom of the vessel and a pressure-reducing valve, into a glass flask immersed in an oil bath at 180° C., surmounted by a short Vigreux column connected to a receiving flask placed in a dry ice bath at −78° C. In this manner 114 g of the product is collected in the receiving flask, which is then left to return to ambient temperature, the major part of the butene as well as a small quantity of hexenes thereby escaping in the gaseous phase. The organic chlorine content of the flashed and stabilised product is less than 1 part per million (ppm) by weight.

The fraction of heavy, non-flashed products which also contains the catalyst residues and a small quantity of polymer represents 3 g.

EXAMPLE 2 (Comparative)

In this example the same working method is used as in example 1 to prepare the complex zirconium solution, to set in action the catalyst in the same autoclave and to execute the ethylene oligomerisation reaction under the same conditions for the same reaction time. At the end of the reaction the same amount of ethyl-2-hexylamine is injected into the autoclave using the same technique as in example 1.

The autoclave is then allowed to cool down and is depressurised by releasing the gaseous products into a gasometer. The autoclave is then opened and the contents, representing 93 g of stabilised liquid product, collected in an inert atmosphere. This product is washed with 20 ml of an aqueous solution of 18% by weight of soda to remove the catalyst residues. The organic chlorine content of the product after washing is equal to 26 ppm.

Compared with example 1, this example of a prior art technique shows the superiority of the invention in the case of the ternary chloride catalyst of zirconium-acetal aluminiumethylsesquichloride.

EXAMPLE 3 (Comparative)

In this example the same working method is used as in example 1 to prepare the complex zirconium solution, to set in action the catalyst in the same autoclave and to execute the ethylene oligomerisation reaction under the same conditions for the same reaction time. At the end of the reaction the autoclave is allowed to cool down and is depressurised by releasing the gaseous products into a gasometer. The autoclave is then opened and the contents, representing 92 g of stabilised liquid product is collected in an inert atmosphere.

$0.2.10^{-3}$ moles of water, that is to say equivalent to the zirconium, is added, while agitating vigorously, to this product which is maintained in an inert atmosphere, then 20 ml of an aqueous solution of 32% by weight ammonia. After decanting and separation of the hydrocarbonic phase, its organic chloride content is determined, which is equal to 54 ppm.

Compared to example 1, this example of another prior art technique shows the superiority of the invention in the case of the ternary chloride catalyst of zirconium-acetal aluminiumethylsesquichloride.

EXAMPLE 4 (Comparative)

In this example the same working method is used as in example 1 to prepare the complex zirconium solution, to set in action the catalyst in the same autoclave and to execute the ethylene oligomerisation reaction under the same conditions for the same reaction time. At the end of the reaction 3 ml of water is injected into the autoclave under pressure, by means of a lock chamber which can be brought to a pressure greater than that of the autoclave. The autoclave is then allowed to cool down and is depressurised by releasing the gaseous products into a gasometer. The autoclave is then opened and the stabilised liquid product is collected.

This product is then distilled and the organic chloride content of each fraction collected is analysed. In this way 21 g of hexenes are obtained which contain 418 ppm of chlorine, 12,5 g of octenes containing 426 ppm of chlorine, 7.3 g of decenes which contain 553 ppm of chlorine and a bottoms product of 10.2 g containing 1,650 ppm of chlorine.

This example shows that with an aqueous treatment of the raw oligomerisation effluent, the chlorinated secondary products are present in all the distilled fractions.

EXAMPLE 5

The oligomerisation reaction of the ethylene is carried out in a continuously operating pilot unit comprising a perfectly agitated reactor with a total volume of 1 litre, operating with a control level of 0.7 litres of liquid. Into this reactor, the temperature of which is regulated at 120° C. by means of oil circulation, and the pressure of which is maintained at 6.5 MPa by virtue of a depressurising valve located on the output line, 25 g per hour of a solution of 0.7 g of sublimated zirconium chloride and 0.9 g of 2,2-bis(2-ethylhexyloxy) propane in 1 kg of dried and de-aerated ortho-xylene, and 25g per hour of a solution of 17.4 g of aluminiumethylsesquichloride in 1 kg of dried and de-aerated ortho-xylene is continuously injected. Under these circumstances, the yield of ethylene entering the reactor, subject to the level control, is determined to be 180 g per hour.

At the reactor output, 30 g per hour of a solution of 44.4 g of laurylamine in 1 kg of dried and de-aerated ortho-xylene is continuously injected in line, corresponding to an amine/Al ration equal to 2.05 molar. The effluent then passes through a flash column operating at a temperature of 150° C. at a pressure of 0.3 MPa. The flashed fraction is sent to a stabilising column, and the non-flashed fraction is collected in a receiving pot. This non-flashed fraction, which also contains catalyst residues with a small quantity of polymer, represents a yield of 23 g per hour. The balance of matter around the stabilising column indicates a yield of flashed oligomers equal to 107 g per hour.

The analysis of organic chloride in the flashed and stabilised fraction shows a value of less than 1 ppm.

EXAMPLE 6 (Comparative)

The same pilot unit is used as described in example 5 and under the same conditions except that the flash column is not used. The effluent treated with laurylamine under the same conditions as in example 5 is thus directly sent to the stabilising column.

The stabilised product collected at the bottom of the column is discontinuously treated with an aqueous solution of 18% by weight of soda, at 2 volumes of product to one volume of soda.

The analysis of the organic chloride in the stabilised and soda-treated product shows a value of 39 ppm.

The comparison of examples 5 and 6 of a continuous operation confirms the unexpected beneficial effect of the sequence of amine treatment and then flash, already demonstrated in a batch operation in examples 1 and 2.

We claim:

1. A method for conversion of ethylene into improved purity light alpha olefines, comprising the steps of:

contacting ethylene with an oligomerization catalyst obtained by mixture:

of a zirconium compound with the formula $ZrX_xY_yO_z$ in which X is an atom of chlorine or bromine, Y is a radical selected from the group consisting of $RO^-$ alkoxys, $R_2N^-$ aminos, and $RCOO^-$ carboxylates, where R is a hydrocarbyl radial having 1 to 30 carbon atoms, x and y can have whole values from 0 to 4 and z equals 0 or 0.5, the sum of x+y+2z being equal to 4, with an organic compound with the formula $(R_1')(R_2')C(OR_1)(OR_2)$ in which $R_1'$ and $R_2'$ are constituted by one atom of hydrogen or a hydrocarbyl radical having 1 to 30 carbon atoms, and $R_1$ and $R_2$ are hydrocarbon radicals having 1 to 30 carbon atoms, and with an aluminum compound with the formula $AlR''_nX_{3-n}$ in which R'' is a hydrocarbyl radical having 1 to 6 carbon atoms, X is an atom of chlorine or bromine, and n is a number between 1 and 2, conducting an oligomerization of said ethylene to produce a raw oligomerization effluent, introducing into the raw oligomerization effluent a deactivating agent consisting essentially of at least one amine and subjecting the resultant deactivated oligomerization effluent to vaporization so that unreacted ethylene and alpha olefin oligomers thereof are collected in the vaporized fraction.

2. A method according to claim 1, wherein in that the amine has the general formula $R_1R_2NH$, in which $R_1$ is hydrogen or a hydrocarbon radical having 1 to 22 carbon atoms, and $R_2$ is a hydrocarbon radical having 1 to 22 carbon atoms.

3. Method according of claim 1, characterised in that the amine has at least 6 carbon atoms.

4. Method according to claim 1, characterised in that the amine is selected from the group consisting of cyclohexylamine, ethyl-2-hexylamine, laurylamine, stearylamine, oleylamine, aniline, N-methyl aniline, dibutylamine, didecylamine, and mixtures of amines produced from tallow, palm oil or copra oil.

5. A method according to claim 4, wherein the quantity of amine introduced is such that the molar ratio between the amine and the aluminium compound is between 1:1 and 10:1.

6. A method according to claim 5, wherein the amine has at least 6 carbon atoms.

7. A method according to claim 5, wherein the deactivating agent is devoid of water.

8. A method according to claim 1, wherein the amine is introduced into the raw oligomerisation effluent at a temperature of 20° to 180° C.

9. A method according to claim 1, wherein the quantity of amine introduced is such that the molar ratio between the amine and the aluminium compound is between 0.1:1 and 20:1.

10. A method according to claim 9, wherein the amine has at least 6 carbon atoms.

11. A method according to claim 1, wherein the vaporization is carried out by increasing the temperature to an extent that the unreacted ethylene and alpha olefin oligomers are collected in the vaporized fraction.

12. A method according to claim 1, wherein the vaporization is carried out by lowering the pressure to an extent that the unreacted ethylene and alpha olefin oligomers are collected in the vaporized fraction.

13. A method according to claim 1, characterised in that at least 90% of the volume of the effluent treated with amine is vapourised.

14. A method according to claim 1, characterised in that the vapourisation temperature is less than or equal to 250° C.

15. A method according to claim 1, wherein the method consists essentially of said steps.

16. A method according to claim 1, wherein the deactivation step directly follows the oligomerization step.

17. A method according to claim 16, wherein the vaporization step directly follows the deactivation step.

18. A method according to claim 1, wherein the vaporization step directly follows the deactivation step.

19. A method according to claim 1, wherein X is an atom of chlorine.

20. A method according to claim 19, wherein the resultant vaporized fraction of alpha olefins contain less than 1 ppm of chlorine.

* * * * *

UNITED STATES PATENT AND TRADEMARK OFFICE
CERTIFICATE OF CORRECTION

PATENT NO. : 5,811,619
DATED : September 22, 1998
INVENTOR(S) : Commereuc, et al It is certified that error appears in the above-identified patent and that said Letters Patent is hereby corrected as shown below:

Column 1, line 15, replace "bromide" with --bromine--.

Column 1, line 17, replace "aminos" with --amines--.

Column 3, line 52, after $1.2.10^{-3}$ insert --moles--.

Column 3, line 62, replace "$4.28\ 10^{-3}$" with --$4.28 \cdot 10^{-3}$ moles--.

Column 4, line 27, replace "gasometer" with --gas meter--.

Column 4, line 45, replace "gasometer" with --gas meter--.

Column 5, line 5, replace "gasometet" with --gas meter--.

Column 5, line 10, replace "12,5" with --12.5--.

UNITED STATES PATENT AND TRADEMARK OFFICE
CERTIFICATE OF CORRECTION

PATENT NO. : 5,811,619
DATED : September 22, 1998
INVENTOR(S) : Commereuc, et al It is certified that error appears in the above-identified patent and that said Letters Patent is hereby corrected as shown below:

Column 6, line 6, replace "aminos" with --amines--.

Signed and Sealed this

Twenty-third Day of February, 1999

Q. TODD DICKINSON

Attest:

*Attesting Officer*     *Acting Commissioner of Patents and Trademarks*